United States Patent [19]

Kaczmarzyk et al.

[11] 4,056,103
[45] Nov. 1, 1977

[54] WRAPPER STRUCTURE FOR TAMPONS CONTAINING SUPERABSORBENT MATERIAL

[75] Inventors: Leonard M. Kaczmarzyk; James J. Hlaban, both of Neenah; Patricia J. McKelvey, Appleton, all of Wis.

[73] Assignee: Kimberly-Clark Corporation, Neenah, Wis.

[21] Appl. No.: 776,635

[22] Filed: Mar. 11, 1977

[51] Int. Cl.² ............................................. A61F 13/20
[52] U.S. Cl. ..................................... 128/285; 128/287
[58] Field of Search ................ 128/270, 285, 290 R, 128/290 P, 290 W, 284; 19/144.5

[56] References Cited

U.S. PATENT DOCUMENTS

| | | | |
|---|---|---|---|
| 3,811,445 | 5/1974 | Dostal | 128/285 |
| 3,815,601 | 6/1974 | Schaefer | 128/285 |
| 3,902,493 | 9/1975 | Baier | 128/270 |
| 3,932,322 | 1/1976 | Duchane | 128/270 X |

*Primary Examiner*—Aldrich F. Medbery
*Attorney, Agent, or Firm*—Daniel J. Hanlon, Jr.; William D. Herrick; Raymond J. Miller

[57] ABSTRACT

An improved wrapper structure for tampons containing superabsorbent material. The wrapper provides the used tampon with a fluid-lubricated surface to ease withdrawal. The wrapper is a fluid-permeable web material having a saline fluid retention capacity sufficient to partially counteract the high capillary suction pressure exerted by superabsorbent fibers in the tampon core and thereby retain enough fluid in the wrapper during use to maintain the surface fibers of the wrapper in soft, lubricous condition.

7 Claims, 3 Drawing Figures

WRAPPER STRUCTURE FOR TAMPONS CONTAINING SUPERABSORBENT MATERIAL

BACKGROUND OF THE INVENTION

Much attention has been paid of late to the development of tampons which contain superabsorbent materials, usually polymeric in nature, having a much greater capacity for fluid per unit weight than the cotton and rayon fibers commonly used as the absorbent media in the most popular commerical tampons now being marketed. The increase in fluid capacity and capillary suction pressure exhibited by these superabsorbent materials in such that only minor amounts, i.e. in the range of 5 – 30%, are needed in conjunction with conventional cotton or rayon fibers to provide tampons of vastly improved capacity and better efficiency per unit weight. These improved tampons are therefore capable of being worn for much longer times than prior art tampons. However, one noticeable shortcoming of the higher capacity tampon not experienced with the conventional tampon products was the fact that withdrawal of the used tampon appeared to be more difficult and have greater frictional drag than conventional tampons. This was particularly noticeable when the superabsorbent tampon was removed early and/or when it contained relatively small amounts of absorbed fluid whereby only a portion of the tampon capacity was utilized. In any event, users have reported a perceivable increase in frictional drag during withdrawal of a tampon containing superabsorbent material as compared to their experience with a coventional tampon. This was first attributed in part to the observed greater swelling of the superabsorbent polymer and a resultant increase in bulk. However, no significant reduction in removal resistance was reported when, in an attempt to decrease bulk, the amount of absorbent material present in the tampon was reduced.

Other attempts to solve the problem included: providing a softer, lower density, and less compressed tampon pledget; providing a narrower pledget; isolating the superabsorbent material in the tampon interior; tapering the withdrawal end of the tampon; using smoother wrapper material to reduce friction, including the use of non-absorbent hydrophobic wrappers of the type employed in non-adherent, quick-release surgical dressings; and even adding a surfactant to such wrappers as a lubricant in an attempt to reduce frictional drag.

None of these modifications significantly reduced the incidence of removal difficulty as reported by test panel users.

A basic assumption which guided much of the work in the development of tampons by those skilled in the art was that a more efficient and more comfortable tampon would be one in which a hydrophobic surface is used which remains as dry as possible until the fluid capacity of the tampon core has been reached. Pointed in this direction is a commerically available tampon which contains superabsorbent material in the core, enclosed in a fluid-permeable hydrophobic, spunbonded polyester web. Examination of used tampons indicated a drier surface was acheived but even though the surface web was smooth and of non-adherent character, removal difficulties remained.

Accordingly, it was found to be somewhat contrary to the many previously proposed solutions to the problem when in accordance with this invention, it was discovered that the removal difficulties associated with tampons containing superabsorbent materials can be substantially reduced by providing a wrapper material for the tampon pledget in which the wrapper structure is such that, while it permits ready transmittal of menstrual fluid into the absorbent core of the tampon during use, the wrapper material itself will retain sufficient fluid in its structure to keep the tampon surface soft and lubricated with moisture and thereby reduce the discomfort and difficulties in removal ordinarily associated with tampons containing superabsorbent components.

SUMMARY OF THE INVENTION

This invention is directed to an improvement in tampons of the type which comprise a highly absorbent core enclosed in a fluid-pervious wrapper and in which the absorbent core contains superabsorbent particulate material in either fibrous or non-fibrous form in an amount sufficient to provide a tampon of greatly enhanced fluid holding capacity per unit of weight. A superabsorbent material is defined as one which has a capillary suction pressure of at least 25 cm. of $H_2O$ when a gram of such material has absorbed 5 ml. of physiological saline solution. The improvement resides in providing a fluid-permeable wrapper whose saline fluid retention capacity as defined herein is such that during use the wrapper structure itself is capable of retaining a minor amount of the absorbed fluid sufficient to maintain the surface fibers in a softened and lubricous condition in spite of the high capillary suction pressure exerted by the superabsorbent material in the tampon core, which suction is normally so strong as to maintain the surface of conventional wrappers, which do not have the herein defined retention capacity, substantially dry. A saline fluid retention capacity factor for the wrapper of 30% or more is useful. A factor of at least 60% is preferred. Fluid retention capacity may be defined as the percent saline solution retained in the wrapper material at equilibrium conditions when said wrapper is in simulated contact with a superabsorbent material containing 100% saline solution by weight. Some wrapper materials which have been found suitable for use in the invention include: an all-rayon fiber nonwoven having a basis weight of at least about 8, but preferably 10 to more than 15 grams per square yard; a scrim reinforced all-rayon fiber web in which the fibrous component has a basis weight of at least about 8 grams per square yard; and a scrim-reinforced web of similar weight in which the web components comprise a mixture of cotton, rayon, and polyester fibers in approximately equal amounts plus about 15% by weight of the superabsorbent material.

DETAILED DESCRIPTION

As indicated in the background section, much of the recent development effort in the absorbent tampon art has been directed toward finding ways to increase the absorbent capacity and fluid-holding power of the tampon per unit weight. Many materials have been developed and proposed for such use. Most of these materials are polymeric in nature and are generally described as superabsorbent materials. All are water-swellable and generally water-insoluble. Included among such materials are: crosslinked cellulose ethers, and carboxymethyl cellulose in particular; crosslinked polyalkylene oxides; crosslinked polyacrylamides; alkali metal salts of polyacrylic acid grafted or copolymerized within cellulose and starch polymeric structures; crosslinked polyurethane hydrogels; alloy fibers of carboxymethyl cellulose and regenerated cellulose; alloy fibers of carboxyalkylated starch and regenerated cellulose; phosphorylated cellulose; cross-linked polystyrene sulfonates; cross-linked polyacrylate salts; and the like.

The insolubilized state for most of these materials is usually obtained through crosslinking and is usually accomplished either by chemical reaction or by heat treatment.

These superabsorbent materials are preferably in fibrous form for use in tampons, but other particulate forms such as fiber clumps, powders, pieces of film, coated particles, and the like, have also been suggested.

A common property of all of the above superabsorbent materials is that they exert a higher capillary suction pressure than is exerted by the other absorbent components with which they are combined.

Figure 1:
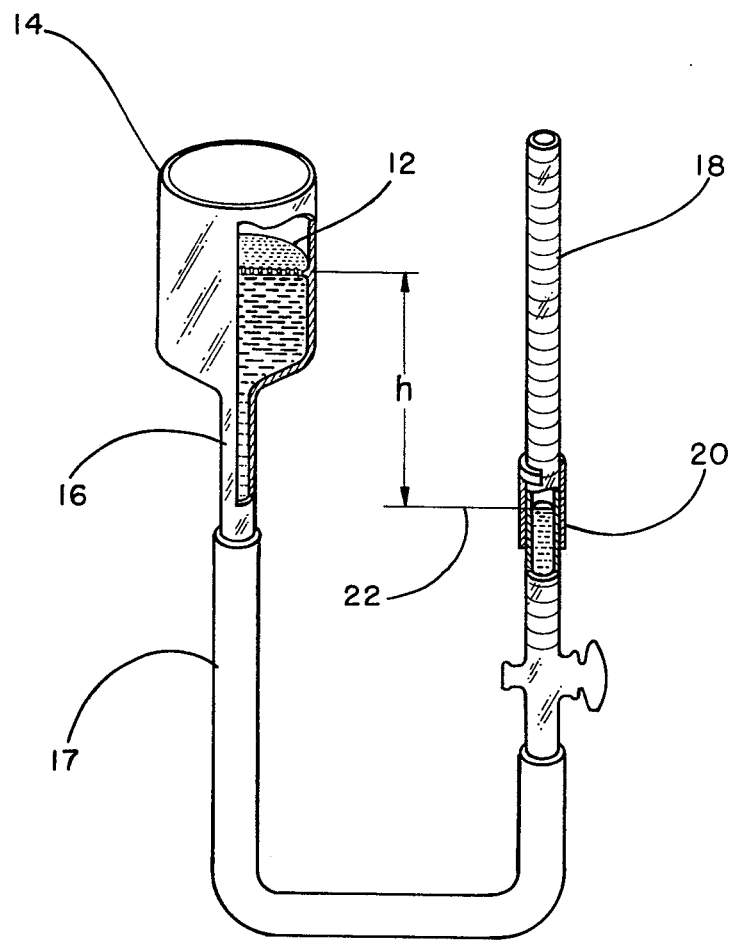
FIG. 1 is a representation, partly in section, of the apparatus used to define the capillary suction pressure of absorbent materials described herein.

The capillary suction pressure of superabsorbent and other fibers may be measured by means of a known capillary tension cell apparatus of the type shown in FIG. 1 of the drawing.

This apparatus comprises a sintered glass, fine frit, filter plate 12 which is an integral part of a glass funnel 14 connected by glass tube 16 to rubber hose 17 which in turn is connected to buret 18. Funnel 14 is attached to a conventional bench stand along with buret 18, which is disposed alongside funnel 14 as shown in the drawing, and held by clamp 20 which permits manual adjustment. When all connections have been made, the device is filled with a physiological saline solution (0.93% NaCl) so that an uninterrupted air-free column of the solution extends from direct contact with the lower face of filter plate 12 through tubing 17 to the desired level of solution 22 in buret 18. Solution level 22 may be set at any predetermined head indicated as value $h$. This predetermined head is maintained substantially constant while testing any one sample by manually moving buret 18 upwardly in clamp 20 as solution is absorbed by the sample. For purposes of testing the superabsorbent material samples mentioned herein and as shown on the accompanying charts, the predetermined suction pressures, or hydrostatic heads used were 60, 40, 25, 20, 15, 10, 5 and 0 cm. of water. While the expression cm. of water is used for simplicity, actual tests were made with physiological saline solution which has a slightly higher density than water.

The superabsorbent material tested in each case is in the form of a dry formed pad 2 inches in diameter and weighing about 0.5 grams, air dry. The pad of material is placed on top of filter plate 12 and covered with a perforated nylon disc weighted to supply light confining pressure of 0.4 p.s.i. on the pad. The physiological saline solution, which has a surface tension of 55 dynes/cm. is used to fill the device. As the pad under test draws solution through filter plate 12 and solution level 22 becomes lower, the hydrostatic head is maintained substantially constant by manually adjusting the buret to the predetermined hydrostatic head setting.

When equilibrium is achieved the volume of solution absorbed is recorded.

Using the above method the following absorbent fibrous materials were tested: FMC 3 denier rayon; FMC 5.5 denier rayon; cotton linters; heat-treated Hercules Aqualon R, a crosslinked carboxymethylcellulose containing free-acid carboxyl radicals; Buckeye CLD (U. S. Pat. No. 3,589,364) a wet crosslinked carboxymethylcellulose in alkali metal salt form; Grain Processing 35A-100 (U. S. Pat. No. 3,661,815) a grafted polymeric starch; phosphorylated cellulose (U. S. Pat. No. 3,658,790); and Dow XD7343.01 (U. S. Pat. No. 3,959,569) a crosslinked partially hydrolyzed polyacrylamide.

Figure 2:
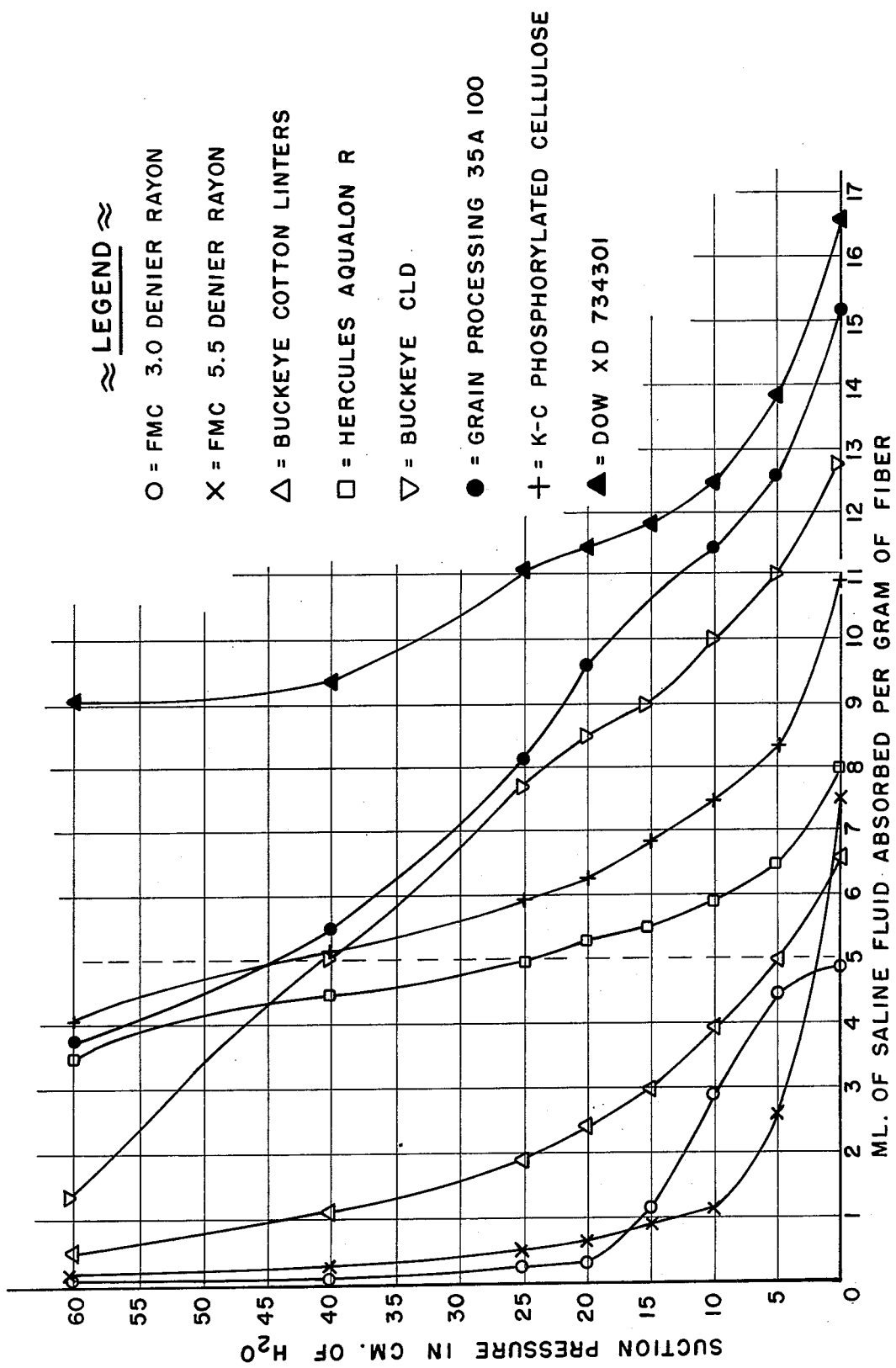
FIG. 2 is a graph comparing absorbency of various materials at various suction pressures.

As noted by reference to graph shown in FIG. 2, rayon and cotton have very low capillary suction pressures while the other crosslinked polymeric materials are all relatively high.

In Table I below, the capillary suction pressures in cm. of $H_2O$ are recorded for each of the tested materials at a suction pressure of 5 ml. of physiological saline solution absorbed per gram of fiber.

TABLE I

| Absorbent Fiber | CAPILLARY SUCTION PRESSURE OF ABSORBENT FIBERS Cm of $H_2O$ Suction Pressure at 5 ml. of Physiological Saline Absorbed per Gram of Fiber |
| --- | --- |
| FMC 3.0 denier rayon | 0 |
| FMC 5.5 denier rayon | 2.5 |
| Buckeye Cotton Linters | 5 |
| Hercules Aqualon R | 25 |
| Buckeye CLD | 40 |
| Grain Processing 35A-100 | 46 |
| KC Phosphorylated Cellulose | 45 |
| Dow XD7343.01 | 60+ |

Figure 3:
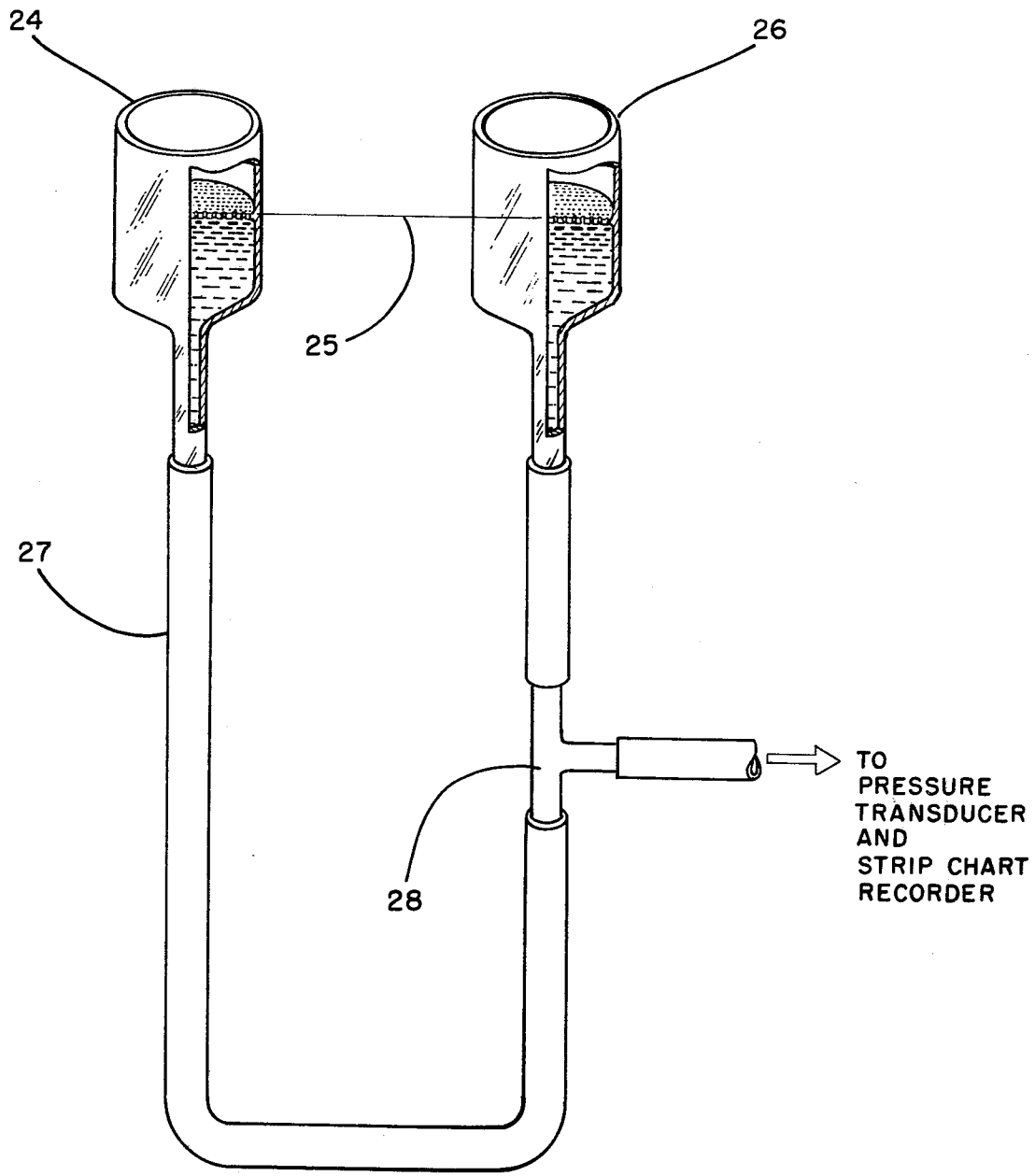
FIG. 3 is a representation, partly in section, of the apparatus used to measure the fluid retention value or capacity of wrapper materials described herein.

The test method used to determine the fluid retention characteristics of wrapper materials when in contact with a tampon core containing superabsorbent material will now be described:

Reference is made to FIG. 3 in which there is shown a suitable apparatus for conducting the tests.

The apparatus consists of two interconnected fine fritter glass funnels 24 and 26 with the glass frit in funnel 24 being at the same level as the glass frit in funnel 26 as indicated by line 25. The rigid plastic tube connecting the funnels is further connected to a pressure transducer and strip chart recorder through glass tee 28.

The wrapper material to be tested is placed on top of frit 24 and covered with a perforated nylon disc weighted to supply a light conforming pressure of 0.4 p.s.i. Two grams of the selected tampon blend, comprising a dry-formed fiber pad of the selected mixture of cotton, rayon and the superabsorbent material is placed on frit 26 in the same manner as the wrapper material and also has a pressure of 0.4 p.s.i. applied.

Two milliliters of saline solution are then poured into the fritter glass funnel 24 containing the wrapper material. The fluid, after saturating the test wrapper material, travels through the tube connecting the funnels to reach the superabsorbent material in funnel 26. After the system is allowed to come to equilibrium, i.e., when there is no pressure change in 15 minutes as indicated by the transducer-recorder, the wrapper sample and tampon blend sample are removed and each is placed into a weighing bottle to have their wet weights recorded. The previously recorded dry weight is then subtracted from the wet weight to obtain the weight of moisture retained. The weight of moisture retained is divided by the dry weight and multiplied by 100 to obtain percent moisture retained or the moisture retention value. The calculated moisture retention value obtained by this method which is intended to simulate capillary conditions in actual use, has been found to correlate closely with the amount of moisture retained in the wrapper when it is in functional contact with the blended core of blended fibers containing superabsorbent material as found in a finished tampon structure. It is this moisture retention value which is used to characterize the moisture retention capacity of the wrapper materials suitable for use in this invention.

Wrapper materials tested by this method included a 13 gram/sq. yd. spunbonded polypropylene, both untreated and with 0.1% wetting agent; a 6 × 5 nylon scrim in combination with a 5 gram/sq. yd. web of 100% comber cotton fibers; a 12 × 5 nylon scrim with a 10 gram/sq. yd. web made up of a blend of fibers comprising 33-⅓% each of cotton, rayon and polyester fibers; a 17 gram/sq. yd. carded web of rayon fibers uniformly bonded by impregnation with an acrylic resin; a 12 × 5 nylon scrim in combination with a 10 gram/sq. yd. web made up of a blend of fibers comprising 27½% cotton, 27½% rayon, 27½% polyester and 17½% superabsorbent fibers; a 12 × 5 scrim with a 10 gram/sq. yd. web of comber cotton; and a 12 × 5 scrim with a 10 gram/sq. yd. web of 1.5 denier rayon fibers.

The nylon used in the 12 × 5 scrim had 30 denier yarns in the warp direction (12 yarns per inch) and 20 denier yarns in the fill direction (5 yarns per inch). The nylon yarns used in the other scrims tested were all 20 denier.

The fluid retention value or capacity of each of these wrapper materials stated in terms of the percent saline solution by weight retained in the material, are given below in Table II.

TABLE II

| FLUID RETENTION OF WRAPPER MATERIALS | |
|---|---|
| Material | Percent of Saline Solution Retained in Material |
| Spunbonded polypropylene 13 gm./sq. yd. | 0% |
| Spunbonded polypropylene 13 gm./sq. yd. with 0.1% Glycomul L. C. wetting agent | 0.25% |
| 6 × 5 nylon scrim with 5 gm./sq. yd. comber cotton | 18% |
| 12 × 5 nylon scrim with 10 gm./sq. yd. blend of 33⅓% each cotton, rayon, polyester | 33% |
| Saturation bonded carded rayon web 17 gm./sq. yd. | 69% |
| 12 × 5 nylon scrim with 10 gm./sq. yd. blend of cotton, rayon, polyester, superabsorbent * | 77% |
| 12 × 5 nylon scrim with 10 gm./sq. yd. web of cotton | 50% |
| 12 × 5 nylon scrim with 10 gm./sq. yd. 1.5 denier rayon | 74% |

* 27½% each of cotton, rayon and polyester and 17½% Aqualon R superabsorbent.

When clinical tests were made comparing tampons containing superabsorbent materials in the core and wrapped with each of the above materials an improvement in ease of removal was noted for the last five on the list as compared to the first three. The results also indicated that the higher the rating for the percent of saline solution retained, the better was the rating of that particular tampon with respect to ease of removal.

In an attempt to determine if these results could be correlated with frictional drag, a bench test was devised in which measurements were taken of the frictional drag of a moistened skin-like membrane when in contact with superabsorbent tampon material containing various amounts of fluid and wrapped in the various types of cover materials previously tested. It was found that the results from these bench tests did not correlate with the clinical tests. In the bench tests some of the materials in the first group of three, which are considered unsatisfactory for use in this invention, had the same frictional resistance as materials in the second acceptable group of five. It is not understood why, when two tampons having substantially the same frictional drag bench test rating under simulated moist conditions are compared with the same tampons in clinical use tests, the tampon having a higher fluid retention capacity has better removal characteristics in actual use. In any event it is known that the wrapper with the higher fluid retention value does provide the easier removal characteristics in actual use, and it is theorized therefore that the moisture retention properties of the wrapper material is the measurable factor which contributes to the usefulness of the invention.

What is claimed is:

1. In a tampon comprised of an absorbent core containing superabsorbent materials and a fluid-permeable wrapper enclosing said core and in which said superabsorbent material has a suction pressure in the range of 25 cm. of $H_2O$ or more when 5 ml. of physiological saline fluid are absorbed per gram of fiber, means for providing ease of withdrawal of the tampon comprising a body fluid lubricable wrapper material having a fluid retention capacity of 30% or more, said fluid retention capacity being the percent saline solution retained in the wrapper material at equilibrium conditions when said wrapper is in simulated contact with a superabsorbent material containing 100% saline solution by weight.

2. The tampon of claim 1 in which the wrapper material has a fluid retention capacity of at least 60%.

3. The tampon of claim 1 wherein said wrapper material comprises a non-woven web in which the components are selected from the group consisting of rayon or cotton fibers or a mixture thereof, a mixture of cotton, rayon and polyester fibers with or without superabsorbent fibers, and any of the above-mentioned fibers or fiber combinations reinforced by a nylon scrim.

4. The tampon of claim 1 wherein said wrapper material comprises a bonded carded rayon web having a weight of from 8 to 17 grams per square yard.

5. The tampon of claim 1 wherein said wrapper material comprises a nylon scrim combined with a web comprised of from 8 to 17 gm./sq. yd. of rayon fibers.

6. The tampon of claim 1 wherein said wrapper material comprises a nylon scrim combined with a web comprised of from 8 to 17 gm./sq. yd. of a blend of equal amounts of cotton, rayon, and polyester fibers.

7. The tampon of claim 1 wherein said wrapper material comprises a web made from a blend of cotton, rayon, polyester and superabsorbent fibers and the weight of said web is from 8 to 17 grams per square yard.

* * * * *